US00PP33940P3

(12) United States Plant Patent
Fouillet

(10) Patent No.: US PP33,940 P3
(45) Date of Patent: Feb. 8, 2022

(54) APPLE TREE NAMED 'R203'

(50) Latin Name: *Malus domestica*
Varietal Denomination: R203

(71) Applicant: IFO S.A.R.L., Seiches sur le Loir (FR)

(72) Inventor: Valérie Fouillet, Saint Sylvain d'Anjou (FR)

(73) Assignee: IFO S.A.R.L., Seiches sur le Loir (FR)

( * ) Notice: Subject to any disclaimer, the term of this patent is extended or adjusted under 35 U.S.C. 154(b) by 0 days.

(21) Appl. No.: 17/300,242

(22) Filed: Apr. 22, 2021

(65) Prior Publication Data

US 2021/0345533 P1 Nov. 4, 2021

(30) Foreign Application Priority Data

Apr. 29, 2020 (FR) ..... 21057

(51) Int. Cl.
*A01H 5/08* (2018.01)
*A01H 6/74* (2018.01)

(52) U.S. Cl.
USPC ..... Plt./161
CPC ..... *A01H 6/7418* (2018.05)

(58) Field of Classification Search
USPC ..... Plt./161
See application file for complete search history.

*Primary Examiner* — Susan McCormick Ewoldt
(74) *Attorney, Agent, or Firm* — Michelle Bos Legal LLC

(57) ABSTRACT

'R203' is a new variety of apple tree selected for its distinctive and flavorful red and yellow-white fleshed fruit, which is well-suited for the fresh market.

9 Drawing Sheets

Latin name: *Malus domestica.*
Variety denomination: 'R203'.

BACKGROUND OF THE VARIETY

'R203' is a new and distinct variety of apple tree (*Malus domestica*) obtained from a controlled cross of 'HY52' (female parent, not patented) x 'Scifresh' (male parent, U.S. Plant Pat. No. 13,888) carried out at Seiches sur le Loir, France in 2003. Seeds obtained from the cross were planted at Seiches sur le Loir, and 'R203' was selected from the resulting seedlings for propagation and further observation. 'R203' was first asexually propagated by grafting at Seiches sur le Loir in 2004, and has since been observed to remain true to type through successive asexually propagated generations.

BRIEF DESCRIPTION OF THE VARIETY

The 'R203' apple tree is distinguished by its sweet red and yellow-white fleshed fruit. Comparisons of 'R203' to its parents and to similar variety 'R201' (U.S. Plant Pat. No. 28,218) are shown in Tables 1, 2 and 3 below.

TABLE 1

Comparison of 'R203' to Female Parent 'HY52-1'

| Characteristic | 'R203' | 'HY52-1' |
|---|---|---|
| Flesh color | Red 45A (50%) and yellow-white 158D (50%) | Red is lighter in tone and less intense |
| Harvest date | 15 days after 'HY52-1' (Nov. 19, 2020) | 15 days before 'R203' |
| Brix | 14 °Brix at harvest | 13 °Brix at harvest |
| Eating quality | More firm, juicy and aromatic | Less firm, juicy and aromatic |

TABLE 2

Comparison of 'R203' to Male Parent 'Scifresh'

| Characteristic | 'R203' | 'Scifresh' |
|---|---|---|
| Skin color | Dark purple red 59A | Red 45A |
| Pattern of overcolor | Solid flush with weakly defined stripes | Weakly defined flush with strongly defined stripes |
| Flesh color | Red 45A (50%) and yellow-white 158D (50%) | Light yellow 4D (100%) |
| Full bloom date | Later (Apr. 18, 2019) | Earlier (Apr. 10, 2019) |
| Storageability | Medium | Very good |

TABLE 3

Comparison of 'R203' to Similar Variety 'R201'

| Characteristic | 'R203' | 'R201' |
|---|---|---|
| Fruit size | Smaller (188 g) | Larger (218 g) |
| Flesh color | Red 45A (50%) and yellow-white 158D (50%) | Red 47A (80%) and white 155C (20%) |
| Leaf blade margin | Serrate | Biserrate |
| Russet on fruit | Weak | Medium |
| Apple scab resistance (Rvi6 gene) | Absent | Present |

BRIEF DESCRIPTION OF THE PHOTOGRAPHS

The accompanying photographs were obtained in 2020 at Seiches sur le Loir, France of trees planted in 2015.

DETAILED BOTANICAL DESCRIPTION OF THE VARIETY

Figure 1:
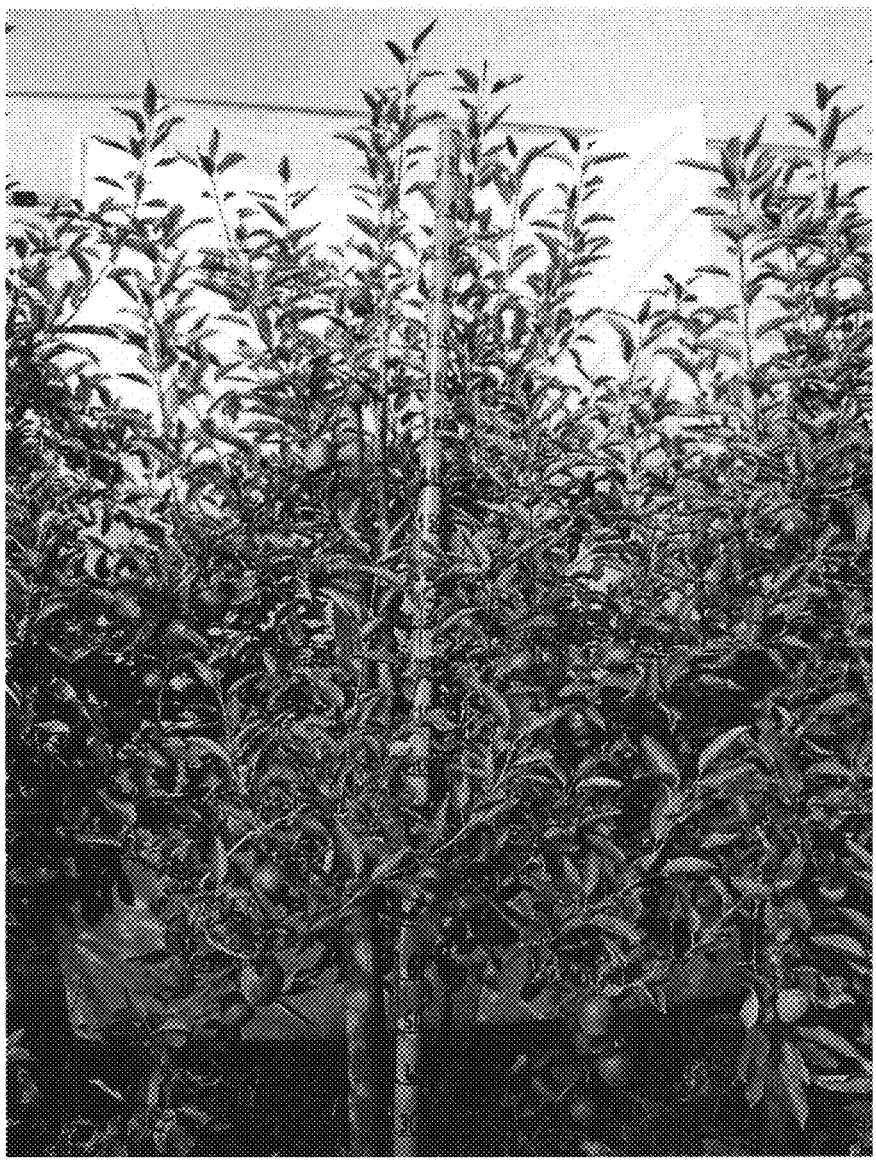
FIG. 1 is a photograph of an 'R203' apple tree with leaves and fruit.
Figure 2:
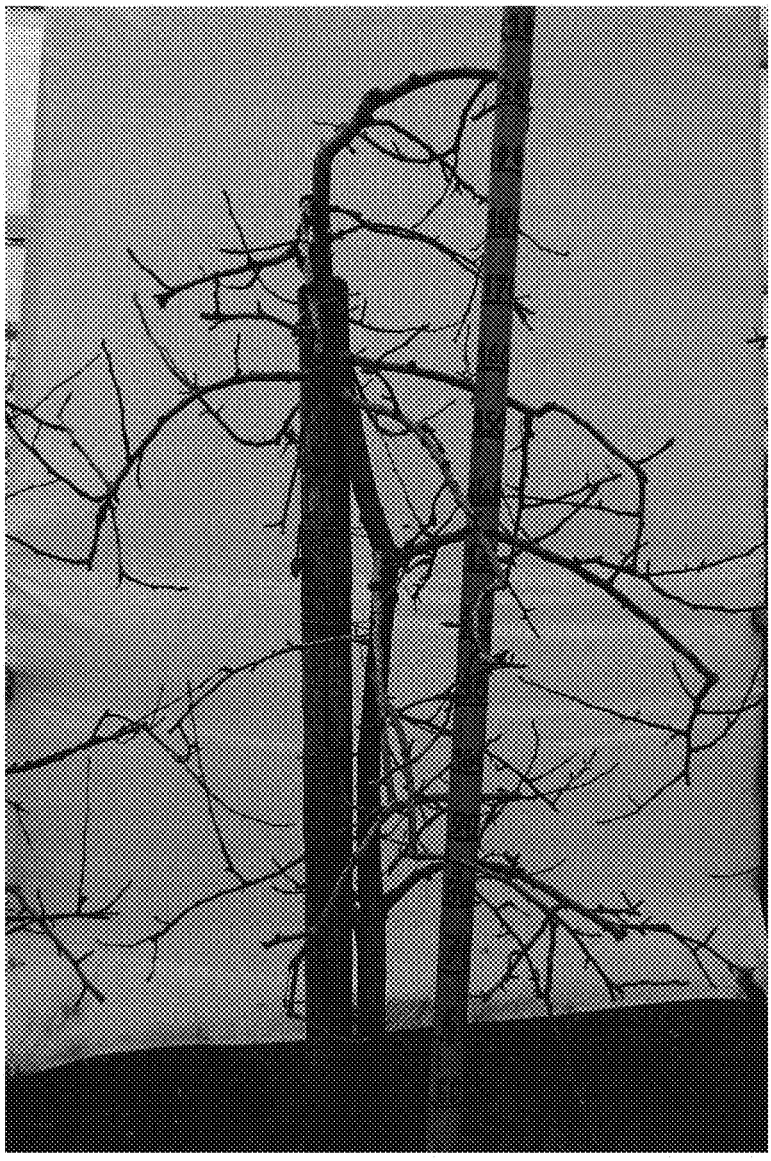
FIG. 2 is a photograph of an 'R203' apple tree.
Figure 3:
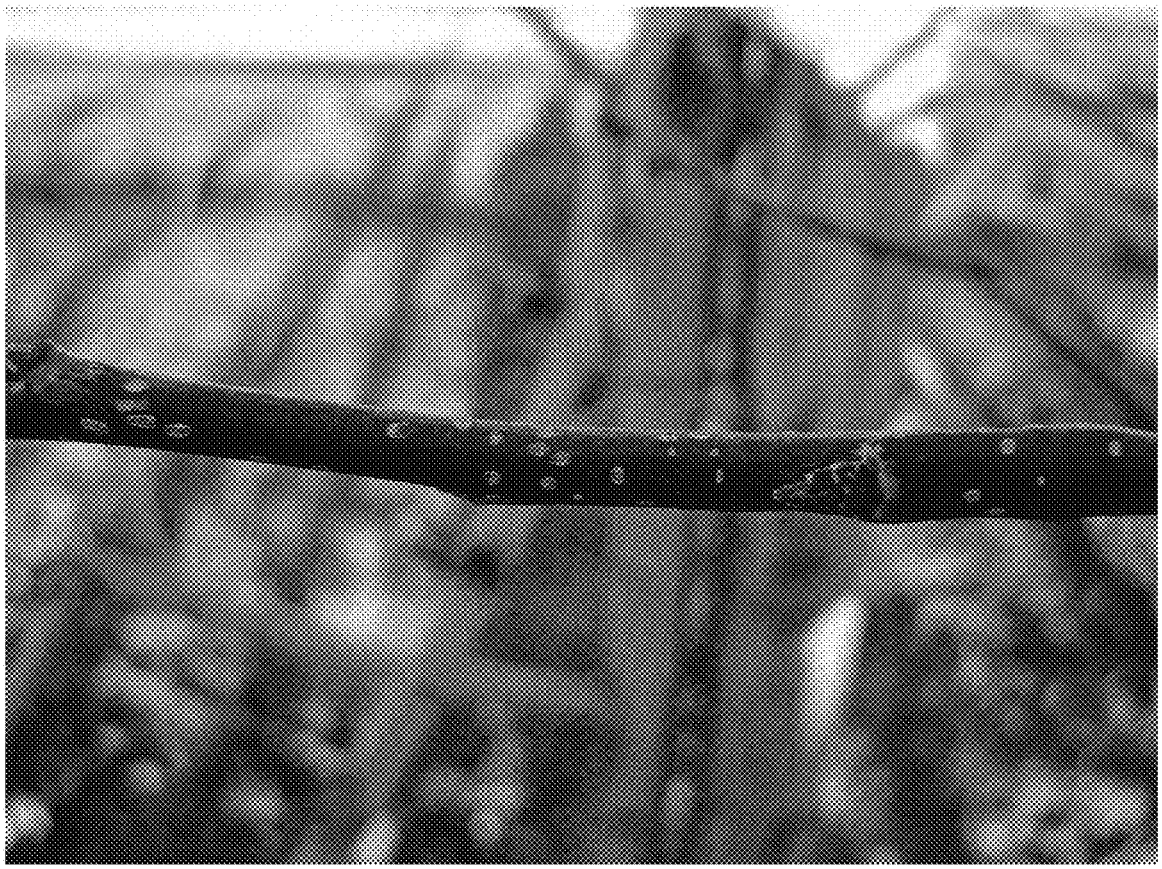
FIG. 3 is a photograph of a one-year-old shoot of an 'R203' apple tree.
Figure 4:
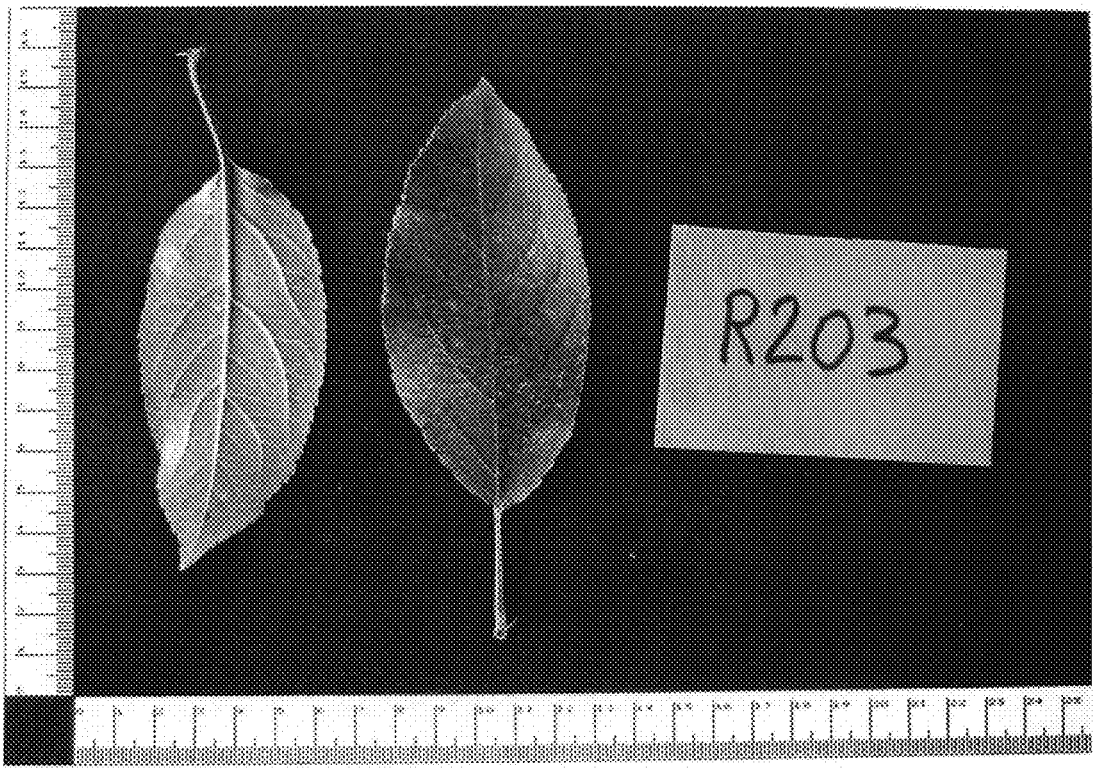
FIG. 4 is a photograph of leaves of an 'R203' apple tree.
Figure 5:
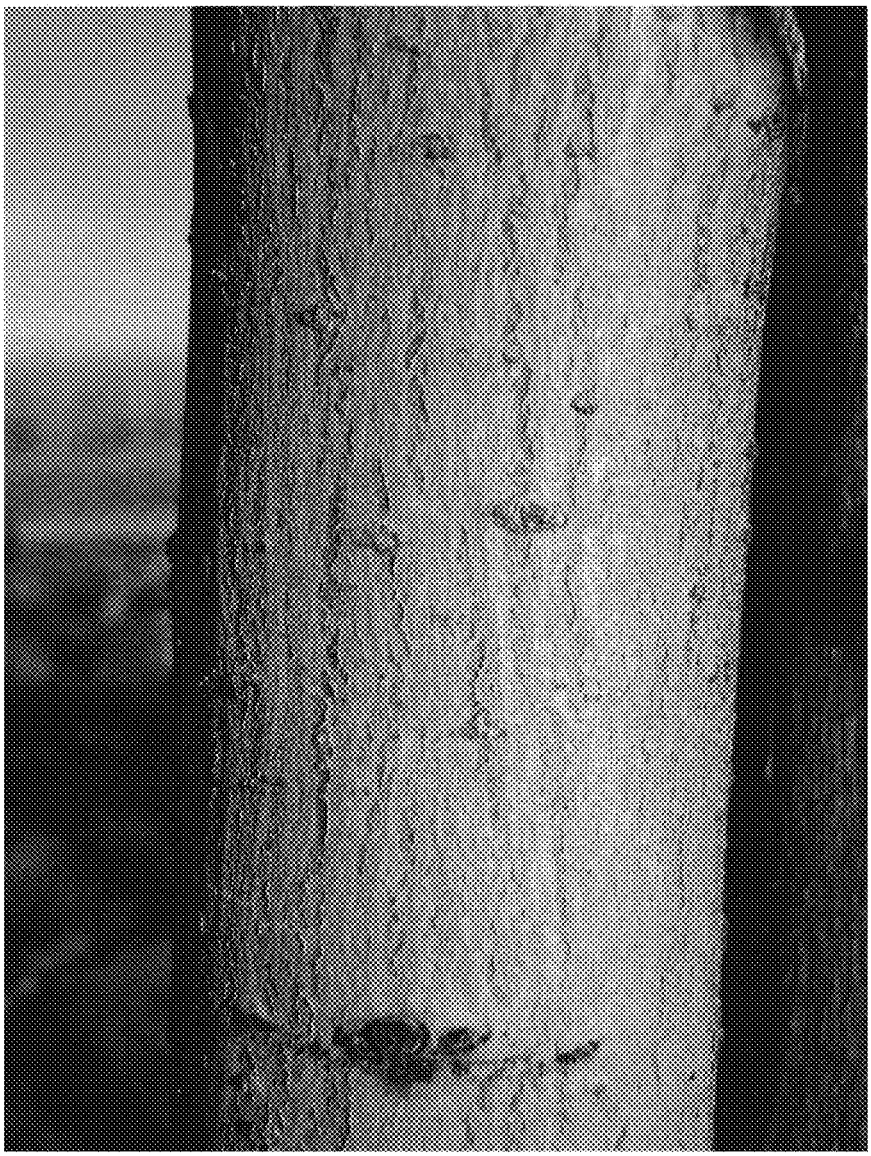
FIG. 5 is a photograph of the trunk of an 'R203' apple tree.
Figure 6:
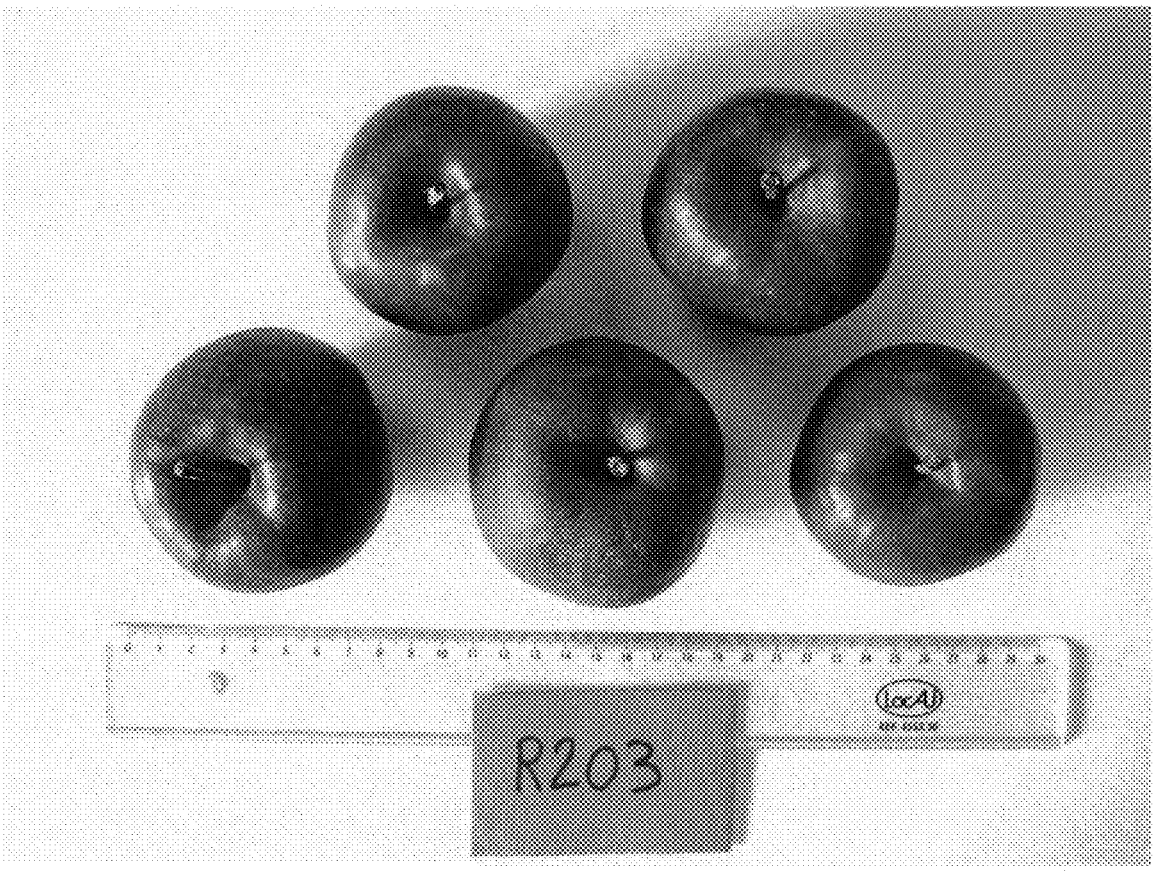
FIG. 6 is a photograph of whole fruit from an 'R203' apple tree.
Figure 7:
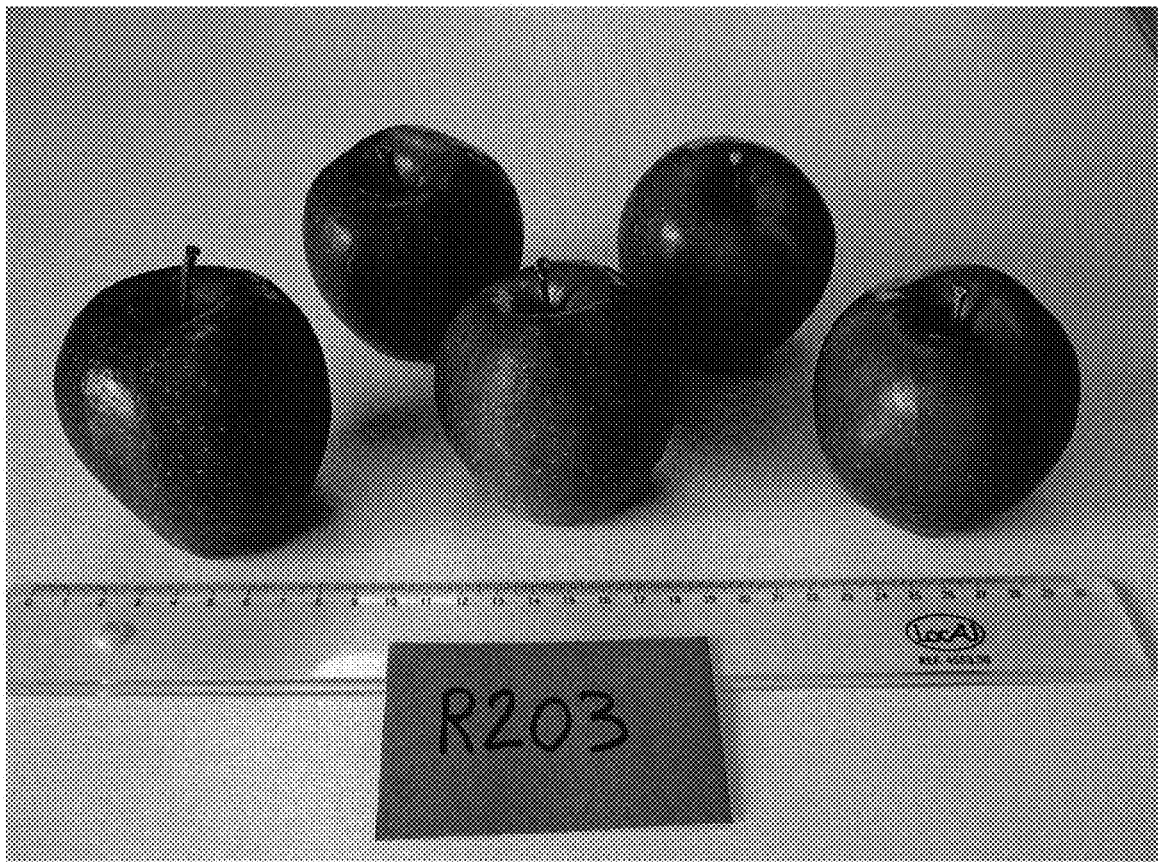
FIG. 7 is a photograph of whole fruit from an 'R203' apple tree.

The following detailed botanical description were obtained at Seiches sur le Loir, France during 2020 (unless otherwise noted), of trees planted in 2015 and grown on Pajam®2 'Cepiland' (U.S. Plant Pat. No. 7,715) rootstock. All colors are described according to The Royal Horticultural Society Colour Chart ($6^{th}$ ed. 2015, reprinted 2019). It should be understood that the characteristics described will vary somewhat depending upon cultural practices and climatic conditions, and will vary with location and season. Quantified measurements are expressed as an average of measurements taken from a number of individual plants of the new variety. The measurements of any individual plant or any group of plants of the new variety may vary from the stated average.

Tree:
- *Vigor*.—Weak to medium.
- *Type*.—Ramified.
- *Habit*.—Drooping.
- *Spread of mature tree*.—1.8 meters.
- *Height*.—2.0 m.
- *Trunk diameter* (*at* 30 *cm above the graft*).—44.2 mm.
- *Bark texture*.—Rough.
- *Bark color*.—Brown N200C.
- *Lenticel length*.—3.7 mm.
- *Lenticel width*.—1.0 mm.
- *Lenticel height*.—0.5 mm.
- *Lenticel shape*.—Medium to very elongated ovate.
- Lenticel color.—Greyed-green 194A.
- *Lenticel quantity*.—Few.

Branch (fruiting branches located at around 1 m above the graft union):
- *Length*.—91 cm.
- *Diameter*.—23.7 mm.
- *Crotch angle*.—80°.
- *Bark color*.—Brown N200C.
- *Lenticel length*.—2.3 mm.
- *Lenticel width*.—1.0 mm.
- *Lenticel height*.—0.5 mm.
- *Lenticel shape*.—Moderately elongated ovate.
- *Lenticel color*.—Greyed-green 194A.

One year old shoot:
- *Length*.—32.2 cm.
- *Diameter*.—3.25 mm.
- *Growth pattern*.—Straight.
- *Color*.—Purple N77A.
- *Pubescence*.—Absent or very weak.
- *Internode length*.—3.7 cm.
- *Lenticel length*.—1.3 mm.
- *Lenticel width*.—1.0 mm.
- *Lenticel height*.—0.1 mm.
- *Lenticel shape*.—Round to slightly elongated ovate.
- *Lenticel color*.—Brown 199C.
- *Vegetative bud shape*.—Conic.
- *Vegetative bud color*.—Purple N77A.

Flower buds:
- *Stage described*.—Bud burst.
- *Quantity per spur*.—3.
- *Bud shape*.—Medium ovate.
- *Apex shape*.—Rounded.
- *Length*.—13 mm.
- *Diameter*.—7 mm.
- *Color*.—Red-purple 59A.

Flowers:
- *Inflorescence type*.—Umbel.
- *Diameter of fully open flower*.—50 mm.
- *Depth of fully open flower*.—13 mm.
- *Relative position of petal margin*.—Touching.
- *Number per cluster*.—5.9.
- *Date of first bloom*.—Apr. 15, 2019; 1 day after 'Golden Delicious'.
- *Date of full bloom*.—Apr. 18, 2019; 1 day after 'Golden Delicious'.
- *Pollination requirement*.—Not known.

Petals:
- *Number per flower*.—5.
- *Petal shape*.—Moderately elongated ovate.
- *Length*.—24 mm.
- *Width*.—13 mm.
- *Apex shape*.—Rounded to acute.
- *Base shape*.—Rounded.
- *Margin*.—Entire.
- *Color of upper surface*.—Red-purple 64B.
- *Color of lower surface*.—Red-purple 64B.
- *Color of venation*.—Red-purple 71A.
- *Petal vein prominence*.—Medium.

Pistils:
- *Length*.—12.8 mm.
- *Color*.—Red-purple 59D.

Stigma:
- *Diameter*.—0.5 mm.
- *Color*.—Greyed-orange 164B.
- *Position of stigma relative to anther*.—Above.

Style:
- *Length*.—7.4 mm.
- *Color*.—Red-purple 59D.

Ovary:
- *Length*.—3.4 mm.
- *Color*.—White NN155C.

Stamens:
- *Quantity*.—17.7 mm.
- *Length*.—8.5 mm.
- *Color of anther*.—Red 49C red and red-purple 64B.
- *Pollen presence*.—Present in moderate quantity.
- *Pollen color*.—Yellow 7D.

Pedicel:
- *Length*.—22.9 mm.
- *Diameter*.—1.5 mm.
- *Color*.—Greyed-purple 183B.

Sepals:
- *Quantity*.—5.
- *Color of upper surface*.—Green 143C.
- *Color of lower surface*.—Greyed-red 178A.
- *Sepal shape*.—Very elongated triangular.
- *Apex shape*.—Acute.
- *Margin* (*smooth, serrated, etc*.).—Entire.

Leaves:
*Shape*.—Elliptical.
*Length*.—101 mm.
*Width*.—48 mm.
*Blade margin*.—Serrate.
*Apex*.—Acute.
*Base shape*.—Acute.
*Profile in cross section*.—Concave.
*Leaf color*.—Upper surface — Green 137A, primary vein red-purple 59A.
*Leaf color*.—Lower surface — Greyed-green 194A.
*Arrangement*.—Alternate.
*Attitude in relation to shoot*.—Upward.

Petiole:
*Length*.—26 mm.
*Diameter*.—2 mm.
*Color*.—Red-purple 59A with greyed-purple 187A near base.

Figure 8:
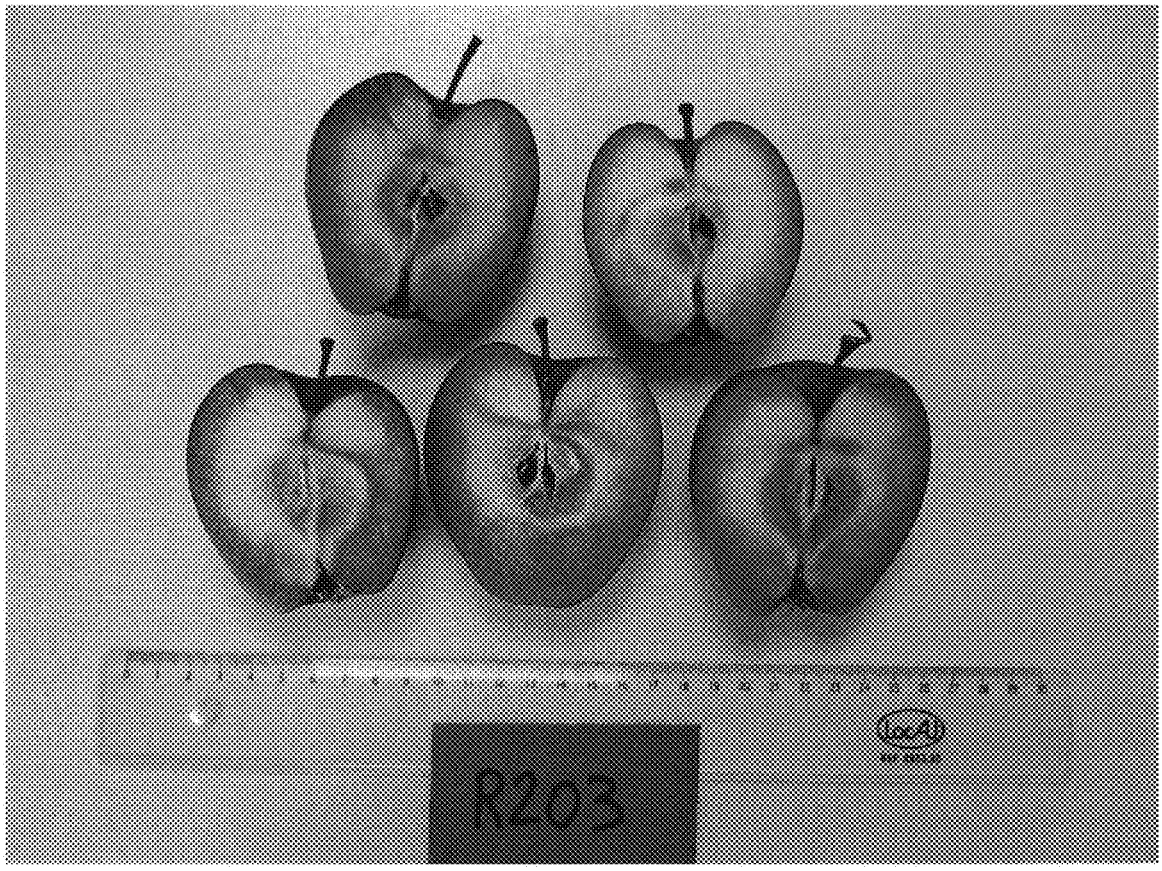
FIG. 8 is a photograph of sectioned fruit from an 'R203' apple tree.
Figure 9:
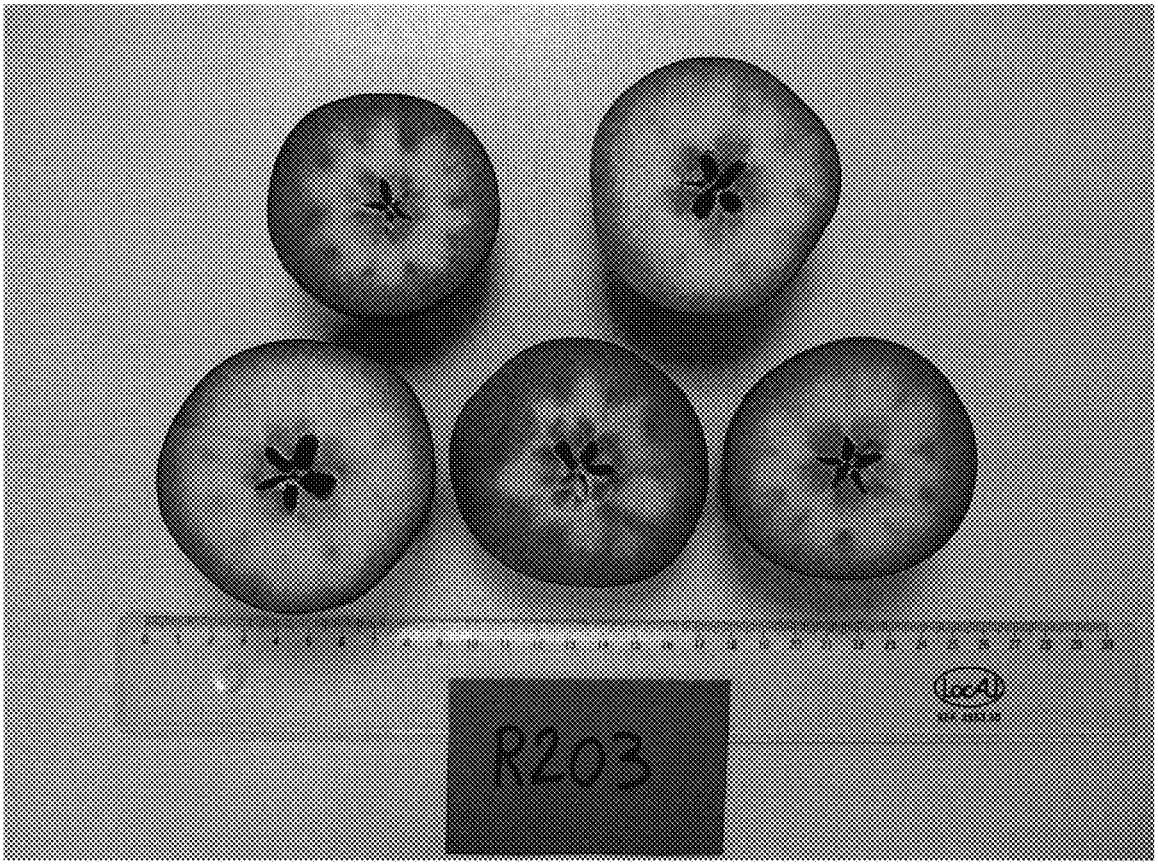
FIG. 9 is a photograph of sectioned fruit from an 'R203' apple tree.

Fruit:
*Diameter*.—72 mm.
*Height*.—73 mm.
*Height to width*.—1:1.
*Weight*.—188 g.
*General shape in profile*.—Conic.
*Position of maximum diameter*.—Moderately toward base.
*Ribbing*.—Weak to medium.
*Crowning at calyx end*.—Weak.
*Bloom of skin*.—Absent or weak.
*Greasiness of skin*.—Weak.
*Background color of skin*.—Orange 26D (after storage).
*Over color of skin*.—Red-purple 59A (after storage).
*Amount of over color*.—90%.
*Intensity of over color*.—Intense.
*Pattern of over color*.—Solid flush with weakly defined stripes.
*Amount of russet around stalk cavity*.—Absent or weak.
*Amount of russet on cheeks*.—Absent or weak.
*Area of russet around eye basin*.—Absent.
*Length of stalk*.—30 mm.
*Diameter of stalk*.—2 mm.
*Stalk color*.—Greyed-purple 183A.
*Depth of stalk cavity*.—17 mm.
*Width of stalk cavity*.—33 mm.
*Depth of eye basin*.—5 mm.
*Width of eye basin*.—28 mm.
*Diameter of eye*.—10 mm.
*Length of sepal*.—6 mm.
*Firmness of flesh*.—7.5 kg/cm$^2$.
*Flesh texture*.—Medium, neither fine nor coarse.
*Number of locules*.—5.
*Locule length*.—10 mm.
*Locule width*.—4 mm.
*Aroma, flavor*.—Aromatic, balanced acid and sugar.
*Juiciness*.—Very juicy.
*Brix*.—13.7 ° Brix.
*Flesh color*.—Red 45A (50%, near the skin and core) and yellow-white 158D (50%); See FIGS. 8 and 9.

Seeds:
*Quantity per fruit*.—Average 6.4.
*Length*.—9.2 mm.
*Width*.—4.6 mm.
*Shape*.—Moderately elongated ovate.
*Color*.—Greyed-orange 166A.

Harvest:
*Harvest date*.—October 13 (2020); one week before 'Fuji'.
*Yield*.—19 kg per tree (2020).
*Number of picks*.—1.

Disease resistance/susceptibility: None noted.
Eating quality: Very good.
Storageability: Moderate.
Market use: Fresh consumption.

The invention claimed is:

1. A new and distinct apple tree named 'R203' substantially as described and illustrated herein.

* * * * *